United States Patent
Greil et al.

(10) Patent No.: US 7,355,041 B2
(45) Date of Patent: Apr. 8, 2008

(54) INTERMEDIATES IN CEFPROZIL PRODUCTION

(75) Inventors: Julia Greil, Kramsach (AT); Johannes Ludescher, Breitenbach (AT); Siegfried Wolf, Brixlegg (AT)

(73) Assignee: Sandoz GmbH, Kundl (AU)

( * ) Notice: Subject to any disclaimer, the term of this patent is extended or adjusted under 35 U.S.C. 154(b) by 80 days.

(21) Appl. No.: 10/485,420

(22) PCT Filed: Jul. 31, 2002

(86) PCT No.: PCT/EP02/08554

§ 371 (c)(1), (2), (4) Date: Jan. 30, 2004

(87) PCT Pub. No.: WO03/011871

PCT Pub. Date: Feb. 13, 2003

(65) Prior Publication Data

US 2004/0192909 A1   Sep. 30, 2004

(30) Foreign Application Priority Data

Aug. 1, 2001   (GB) ................................. 0118764.0

(51) Int. Cl.
*C07D 501/22* (2006.01)
*C07D 501/04* (2006.01)

(52) U.S. Cl. ..................................... 540/215

(58) Field of Classification Search ..................... None
See application file for complete search history.

(56) References Cited

U.S. PATENT DOCUMENTS

| 4,336,376 A | 6/1982 | Coll et al. |
| 4,619,925 A | 10/1986 | Hoshi et al. |
| 4,659,814 A | 4/1987 | Palomo-Coll et al. |
| 5,908,929 A | 6/1999 | Nair et al. |
| 6,333,409 B1 * | 12/2001 | Ludescher et al. .......... 540/215 |
| 6,903,211 B2 * | 6/2005 | Deshpande et al. ......... 540/215 |
| 7,230,097 B2 * | 6/2007 | Tyagi et al. ................ 540/215 |

FOREIGN PATENT DOCUMENTS

| EP | 0523585 | 1/1993 |
| WO | WO 98 04732 A | 2/1998 |
| WO | WO 01 30783 A | 5/2001 |

OTHER PUBLICATIONS

Amidine <http://en.wikipedia.org/wiki/Amidine> downloaded from the Internet Jan. 9, 2006.*
Kemperman GJ et al: Synthesis of cephalosporin-type . . . asymmetric transformation. European Journal of organic chemistry, vol. 2001, No. 10, 2001, pp. 1817-1820.

* cited by examiner

*Primary Examiner*—Mark L. Berch
(74) *Attorney, Agent, or Firm*—Luedeka, Neely & Graham, P.C.

(57) ABSTRACT

A salt of PACA with an amidine and its use in the production of cefprozil.

10 Claims, No Drawings

INTERMEDIATES IN CEFPROZIL PRODUCTION

The present invention relates to intermediates in cephalosporin production.

Cefprozil [6R-[6α,7β(R*)]]-7-[[amino(4-hydroxyphenyl)acetyl]amino]-8-oxo-3-(1-propenyl)-3-thia-1-azabicyclo[4.2.0]oct-2-ene-2-carboxylic acid, e.g. in the form of a monohydrate (see e.g. The Merck Index, 12$^{th}$ edition, item 1992), is a broadly used cephalosporin antibiotic.

We have now found a simple and economic process, e.g. useful on technical scale; for the production of cefprozil, e.g. in the form of a monohydrate, e.g. in pure form.

In one aspect the present invention provides a process for the production of cefprozil, e.g. in the form of a solvate, e.g. hydrate, such as a monohydrate, comprising the steps A1) reacting PACA of formula

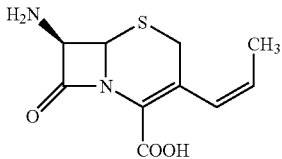

III in the form of a salt with an amidine, e.g. a compound of formula

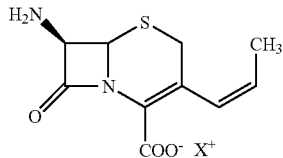

I wherein
X$^+$ is a group of formula

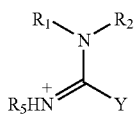

II and either
a) Y is a group of formula —NR$_3$R$_4$ and
  a1) R$_1$ to R$_5$ are the same or different and are independently of each other hydrogen, alkyl or aryl; or
  a2) two of the substituents R$_1$, R$_2$ and R$_5$, and/or R$_3$ and R$_4$ together form a —(CH$_2$)$_2$— or —(CH$_2$)$_3$— group; and the other substituents R$_1$ to R$_5$ are as defined above; or
b) Y forms together with R$_2$ a —(CH$_2$)$_3$— or —(CH$_2$)$_5$— group, and R$_1$ and R$_5$ together form a —(CH$_2$)$_3$— group, with a mixed carboxylic acid anhydride of an α-amino-p-hydroxyphenylacetic acid, and B1) isolating ceprozil from the reaction mixture obtained in step A1); and optionally C1) converting cefprozil isolated in step B1) into ceprozil in the form of a monohydrate.

In another aspect the present invention provides a process for the production of cefprozil, e.g. in the form of a solvate, e.g. N,N-dimethylformamide (DMF) solvate (e.g. cefprozil x1.5 DMF) or hydrate, e.g. monohydrate, which comprises the steps
  A2) producing a mixed carboxylic acid anhydride by acylating a vinyl substituted α-amino-p-hydroxyphenylacetic acid with an appropriate acylating agent,
  B2) reacting a mixed carboxylic acid anhydride obtainable in step A2) with PACA in the form of a salt with an amidine, e.g. a compound of formula I wherien X$^+$ is as defined above,
  C2) isolating cefprozil, e.g. in the form of a solvate, e.g. N,N-dimethylformamide solvate, e.g. in crystalline form; obtained in step B2), and optionally
  D2) converting cefprozil obtained in step C2), e.g. in the form of an N,N-dimethylformamide solvate; into cefprozil in the form of a hydrate; e.g. a monohydrate.

A process according to the present invention may be carried out as appropriate, e.g. according to, e.g. analogously, to a method as conventional, and is preferably carried out as follows:

Step A1), or step B2), respectively, is an acylation reaction with a mixed carboxylic acid anhydride.

An appropriate mixed carboxylic acid anhydride is preferably provided according to step A2), i.e. by acylating, e.g. reacting, an N-vinyl substituted α-amino-p-hydroxyphenylacetic acid, with an appropriate acylating agent. For that acylation the N-substituted vinyl α-amino-p-hydroxyphenylacetic acid may be used in free form or in the form of a salt, e.g. including a Dane salt, such as sodium or potassium D-N-(1-methoxycarbonylpropen-2-yl)-α-amino-p-hydroxyphenylacetate, or sodium or potassium D-N-(1-ethoxycarbonyl-propen-2-yl)-α-amino-p-hydroxyphenylacetate. Appropriate acylating agents include aliphatic, alicyclic, or aromatic acids, e.g. including alkanoic acids, such as chloroformic acid, pivalic acid, 2-ethylhexanoic acid, benzoic acid, e.g. in a reactive form. A reactive form includes acid halogenides, e.g. chlorides, e.g. including pivaloyl chloride, 2-ethyl-hexanoyl chloride, benzoyl chloride and esters, e.g. chloroformic acid alkyl esters, such as ethyl chloroformate. In step A2) a small amount of a free C$_4$-C$_9$ acid may be present, e.g. an alkanoic acid such as pivalic acid or 2-ethylhexanoic acid, or an aromatic acid, e.g. benzoic acid, preferably 2-ethylhexanoic acid or pivalic acid, e.g. which may catalyze the mixed carboxylic acid anhydride formation. The side chain of said free carboxylic acid may be the same or different to that of the acylating agent and is preferably the same. Appropriate solvents in step A2) include halogenated hydrocarbons e.g dichloromethane or acetic acid (C$_{1-4}$)alkylesters such as butylacetate or isopropylacetate. A co-solvent may be present which may improve or activate the reaction of above Dane salts with the acylating agent, such as organic amides, e.g. in the form of N-subsituted amides, e.g. including formamide, acetamides, N-mono or N,N-dimethyl amides, such as N,N-dimethyl formamide (DMF), N-methylacetamide, N,N-dimethylacetamide; pyrrolidines, such as N-methylpyrrolidines; ureas, e.g. tetramethylurea, branched chain alkyl alcohols, such as isopropanol; preferably DMF. Preferably a base, e.g. a tertiary amine base, may be present as a catalyst in step A2). A preferred base includes pyridines, for example a picoline, e.g. 3- or 4-picoline, or a lutidine. The formation of the mixed carboxylic acid anhydride in step A2) may be effected at temperatures as appropriate, e.g. including temperatures from −50° to 50° C., preferably from −40° C. to 0° C. A solution or a suspension of a mixed carboxylic acid anhydride may be obtained which may be used further, e.g. in step A1) or B2), as such, e.g. without isolation of the mixed carboxylic acid anhydride, e.g. which solution or a suspension may be stored, e.g. at appropriate temperatures, e.g. including temperatures from (ca.) −60° C. to −20° C.

Step A1), or, step B2), respectively, is an acylation reaction of the amine group of a PACA-amidine with a mixed carboxylic acid anhydride, e.g. obtainable according to step A2). PACA in the form of a salt with an amidine, e.g. a compound of formula I, wherein $X^+$ is as defined above, is novel.

In another aspect the present invention provides PACA of formula

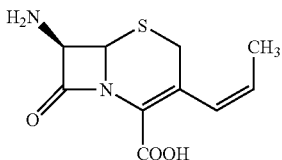

III in the form of a salt with an amidine, e.g. a compound of formula I as defined above wherein $X^+$ is as defined above, e.g. in the form of an acid addition salt or in the form of a solvate of a compound of formula I or in the form of a solvate of an acid addition salt of a compound of formula I.

In another aspect the present invention provides the use of a compound according to the present invention, e.g. as an Intermediate, in the production of cefprozil.

PACA in the form of a salt(s) with an amidine according to the present invention is hereinafter designated as "PACA-amidine(s)".

PACA-amidines may exist in free form, in the form of a salt, in the form of a solvate and in the form of a salt and a solvate. PACA-amidines in free form may be converted into PACA-amidines in the form of a salt and vice versa. PACA-amidines in the form of a solvate or in the form of a salt and a solvate may be converted into PACA-amidines in unsolvated form or PACA-amidines in the form of a salt in unsolvated form and vice versa.

PACA-amidines are e.g. useful in a process for the production of ceprozil according to the present invention and may be stable soluble forms of PACA in a solvent or solvent mixtures which may allow further reacting, e.g. acylating the amine group in position 7 of the ring structure, easily, e.g. without the need to solubilize PACA either by silylation or the use of complex solvent mixtures. PACA-amidines may be stable despite the high basicity of the corresponding bases, e.g. with respect to degradation and with respect to Z/E isomerization; and additionally may be soluble in a number of solvents or solvent mixtures and may thus allow to choose solvents or solvent mixtures in a further reaction step, which easily may be recycled from a reaction mixture obtained in said further reaction step, e.g. in a process for the production of cefprozil.

PACA-amidines include PACA amidine salts and guanidine salts, which guanidines being amino-amidines, having an amidine structure and carrying a further amine group at the carbon atom of the —N═C—N— group. Appropriate guanidine salts include e.g. compounds of formula II, wherein Y denotes a group of formula —$NR_3R_4$ wherein R3 and R4 are as -defined above.

If not otherwise defined herein any carbon atom containing group preferably may contain up to 20 carbon atoms. Aryl includes phenyl, naphthyl. Any group may be unsubsfltuted or substituted, e.g. substituted as appropriate, e.g. according, e.g. analogously, as conventional in organic chemistry, e.g. β-lactam chemistry, such as cephalosporin chemistry. A solvent includes a solvent mixture (system) of individual solvents, e.g. as correspondingly indicated.

In a compound of formula II preferably Y is a group of formula —$NR_3R_4$ and $R_1$ to $R_5$ are independently of each other hydrogen, unsubstituted alkyl or alkyl substituted by a phenyl group, for example benzyl, or unsubstituted aryl; preferably $R_1$, $R_2$, $R_3$ and $R_4$ are $(C_{1-4})$alkyl and $R_5$ is hydrogen; or Y together with $R_2$ form a —$(CH_2)_3$— or —$(CH_2)_5$— group, and $R_1$ and $R_5$ together form a —$(CH_2)_3$— group. Preferred PACA-amidines include PACA in the form of a salt with tetramethylguanidine (TMG), 1,8-diazabicyclo[5.4.0]undec-7-ene (DBU), 1,5-diazabicyclo[4.3.0]non-5-ene (DBN).

The production of a PACA-amidine salt is a salt formation process which may be carried out as appropriate, and is preferably carried out as follows:

PACA may be suspended in an appropriate solvent and an amidine is added. An appropriate solvent system is described below for providing a solution of a PACA-amidine. A solution may be obtained, e.g. if PACA is in the form of a salt with a guanidine which guanidine is in the form of a free base. The ratio of PACA and an amidine is not critical. E.g. per equivalent PACA 1 to 2, e.g. 1 to 1.5, preferably 1 to 1.2 equivalents of an amidine may be used. From the mixture obtained a PACA-amidine may be isolated in the form of a solid, e.g. an amorphous powder, foam, e.g. solvent may be evaporated off and the evaporation residue may be treated with an anti-solvent. An anti-solvent is a solvent wherein a PACA-amidine is less soluble than in a solvent, e.g. including ethers, e.g. tert. butyl-methylether, diethylether, or hydrocarbons, e.g. hexane. A PACA-amidine may be isolated as appropriate, e.g by solvent decantation or filtration.

An appropriate solvent system for providing a solution of a PACA-amidine and for providing PACA-amidines includes e.g. halogenated hydrocarbons, preferably dichloromethane, alkanols, e.g. $(C_{1-4})$ alkanols, such as ethanol, butanol, isopropanol, preferably a $(C_{3-4})$alkanol, such as butanol, for example n-butanol, iso-butanol, tert.-butanol or sec.-butanol, or isopropanol, e.g. isopropanol; optionally in combination with a solvent as described above in step A2). Optionally water may be present.

In another aspect the present invention provides a process for the production of PACA in the form of a salt with an amidine comprising suspending PACA of formula III in an appropriate solvent, adding an amidine and isolating PACA in the form of a salt with an amidine.

For carrying out step A1), or, step B2), respectively, conveniently a solution of a PACA-amidine, e.g. obtainable as described above, may be reacted with, e.g. may be added to, a reaction mixture comprising a mixed carboxylic acid anhydride, e.g. obtainable according to step A2). If desired a small amount of water may be present in the solvent (system). If desired a small amount of a $(C_{4-9})$alkanoic acid, e.g. including 2-ethylhexanoic acid, may be added to a mixture of a PACA-amidine and solvent (system). Appropriate reaction temperatures include e.g. about −60° C. to room temperature, preferably −50° C. to −15° C. Cefprozil, e.g. in a protected form, may be obtained. Cefprozil in a protected form e.g. includes cefprozil, wherein the amine group of the glycyl group attached to the amine group in position 7 of the ring structure, is protected by a substituted vinyl group, e.g. according to a Dane salt used in the production of a mixed anhydride, e.g. as described above in step A2.

If ceprozil is obtained in a protected form cefprozil may be deproteced, e.g. a substituted vinyl group may be split off as appropriate, e.g. by hydrolysis in aqueous acid. Cefprozil may be obtained and may be isolated.

Step B1), or C2), respectively, i.e. the isolation of cefprozil, may be carried out as appropriate and is preferably carried out as follows:

The reaction mixture obtained in step A1) or B2), respectively, may be worked up as appropriate and cefprozil may be isolated as appropriate, e.g. according, e.g. analogously, to a method as conventional. Cefprozil is preferably isolated in the form of a solvate, e.g. in the form of an N,N-dimethylformamide solvate (1/1.5), e.g. in crystalline form, by crystallization of the N,N-dimethylformamide solvate (DMF-solvate) from aqueous, or aqueous/alkanolic respectively, solution by addition of DMF and pH adjustment within 4.5 to 7. Formation of cefprozil in the form of a DMF-solvate, e.g. in crystalline form, is e.g. described in U.S. Pat. No. 4,694,079 which is introduced herein by reference.

Step C1) or D2), respectively, i.e. conversion of cefprozil, e.g. in the form of a DMF-solvate, into cefprozil in the form of a hydrate, e.g. monohydrate may be carried out as appropriate and is preferably carried out as follows:

Cefprozil, e.g. in the form of an DMF-solvate (e.g. 1/1.5) may be mixed with water and an inorganic acid, e.g. hydrochloric acid; e.g. dissolution of cefprozil may be facilitated by addition of said inorganic acid. From the mixture obtained cefprozil in the form of a hydrate, e.g. a monohydrate may be crystallized by addition of an inorganic base, e.g. including sodium hydroxide or aqueous ammonia to adjust a pH which is around the isoelectric point of cefprozil, e.g. at appropriate temperatures, e.g. including temperatures of room temperature or above, e.g. room temperature to 60° C., such as 30° C. to 50° C. Alternatively cefprozil, e.g. in the form of an DMF-solvate, may be converted into cefprozil in the form of a monohydrate by heating a solution or suspension in water at elevated temperates, e.g. including temperatures of 30° C. to 60° C.

Ceprozil in the form of a hydrate, e.g. monohydrate, e.g. in crystalline form may be isolated from the reaction mixture as appropriate, e.g. by filtration, centrifugation.

In the following examples all temperatures are in degree Centigrade and are uncorrected.

The following abbriviations are used:

| | |
|---|---|
| DMF: | N,N-dimethylformamide |
| TMG: | tetramethylguanidine |
| DBU: | 1,8-diaza-bicylo-(5.4.0)undec-7-ene |
| DBN: | 1,5-diaza-bicylo-(4.3.0)non-5-ene |
| PACA: | a compound of formula III as defined above |
| ETHER: | tert. butyl-methylether |

DMF-solvate: cefprozil in the form of a solvate with DMF

EXAMPLE 1

Production of Cefprozil a) Mixed Carboxylic Acid Anhydride Formation

To a mixture of 78.1 ml of $CH_2Cl_2$, 49.7 ml of DMF and 0.3 ml of 4-picoline, 30.24 g of potassium D-N-(1-methoxycarbonylpropen-2-yl)-α-amino phenylacetate are added. The suspension obtained is stirred at room temperature and is cooled to −30°. To the mixture obtained 12.42 ml of pivaloylchloride are added and the suspension obtained is stirred at a temperature of −20° to −25°, cooled to −50° C. and diluted by addition of 41.8 ml of cold DMF.

b) PACA in the form of a salt with TMG

A suspension of 148 ml of $CH_2Cl_2$ and 20.77 g of PACA is cooled to −10° and 11.43 ml of TMG are added. The suspension obtained is warmed up and a solution is obtained. The solution obtained is cooled to −50°.

c) Acylation Reaction of the Free Amine Group in PACA in the Form of a Salt with TMG The solution obtained in step 1b) is added to the suspension obtained in step 1a) at a rate that the temperature does not exceed −40° and the mixture obtained is stirred at −45° for ca. 1 hour and at −35° for ca. 2 hours. Cefprozil wherein the amine group of the glycyl group attached to the amine group in position 7 of the cephalosporin ring structure is protected by a 1-methoxycarbonylpropen-2-yl group is obtained.

d) Cefprozil in the Form of a DMF-solvate

The mixture obtained in step 1c) is added to a mixture of 81 ml of ice water and 18 ml of concentrated HCl and the mixture obtained is stirred. Two phases obtained are separated. To the aqueous layer obtained 180 ml of DMF are added and the pH of the mixture obtained is adjusted with 25% aqueous ammonia to 2.5 at a temperature of ca. 30°. To the mixture obtained 44 ml of DMF are added and the pH is adjusted to 4.2 with 25% aqueous ammonia. To the mixture obtained seed crystalls of a DMF-solvate, i.e. cefprozil x(1/1.5) DMF solvate are added. Cefprozil in the form of a cefprozil x(1/1.5) DMF solvate crystallizes. The pH of the suspension obtained is adjusted to 6.8 and the suspension is allowed to stand at 30°. Cefprozil in the form of a cefprozil x(1/1.5) DMF solvate in crystalline form is filtrated off, washed and dried.

e) Cefprozil in the Form of a Monohydrate 56.3 ml of $H_2O$ are heated to 48°. 40 g of cefprozil in the form of a cefprozil x(1/1.5) DMF solvate are added with stirring. The suspension obtained is stirred, slowly cooled down and kept at about 5°. Cefprozil in the form of a monohydrate crystallizes, is filtrated off, washed and dried.

EXAMPLE 2

PACA in the Form of a Salt with TMG 12.01 g of PACA are suspended in 120 ml of $CH_2Cl_2$, the mixture obtained is cooled in an ice bath and 1.1 equivalents of TMG are added. A solution is obtained, concentrated in vacuo and the evaporation residue is treated with ETHER. Solvent is decanted and the decantation residue is dried. PACA in the form of a salt with TMG is obtained in the form of an amorphous powder. $^1$H-NMR($CDCl_3$, TMS): 1.74 (3H, dd, $CH_3$ of PACA), 2,97 (12H, s, $CH_3$ of TMG), 3,36 and 3,62 (1H, AB, S—$CH_2$—, H-2), 4.62 (1H, d, CH, H-7), 5,00 (1H, d, CH, H-6), 5.52 (1 H, dq, =CH—CH₃ of PACA), 6.39 (1H, d(m), CH= of PACA).

EXAMPLE 3

PACA in the form of a salt with DBU 12.01 g of PACA are suspended in 120 ml of CH₂Cl2, the mixture obtained is cooled in an ice bath and 1.1 equivalents of DBU are added. A solution is obtained, concentrated in vacuo, the concentration residue is treated with ETHER, the solvent is decanted and the decantation residue obtained is dried. PACA in the form of a salt with DBU is obtained in the form of an amorphous powder. $^1$H-NMR(CDCl₃, TMS): 1.60-1.80 (9H, M, CH₃ PACA, 3×C—CH₂—C of DBU), 1.99 (2H, tt, C—CH₂—C of DBU), 2.87 (2H, M, C—CH₂—C of DBU), 3,33-3,64 (8H, M, S—CH₂—, H-2, 3×C—CH₂—N of DBU), 4.62 (1H, D, CH, H-7), 5.01 (1H, D, CH, H-6), 5.55 (1H, d(m), CH=double bonds), 6.39 (1H, Dq, =CH—CH₃).

EXAMPLE 4

PACA in the Form of a Salt with DBN 12.01 g of PACA are suspended in 120 ml of CH₂Cl₂, the mixture obtained is cooled in an ice bath and 1.1 equivalents of DBN are added. A solution is obtained, concentrated in vacuo, the concentration residue is treated with ETHER, solvent is decanted and the decantation residue is dried. PACA in the form of a salt with DBN in the form of an amorphous powder is obtained. $^1$H-NMR(CDCl₃, TMS): 1.74 (3H, dd, CH₃ PACA), 2.00 (2H, tt, C—CH₂—C DBN), 2.12 (2H, tt, C—CH₂—C of DBN), 3.10 (2H, t, C—CH₂—C of DBN), 3.37 (2H, t, C—CH₂—N DBN), 3.46 (2H, t, C—CH₂—N DBN), 3.58 (2H, t, C—CH₂—N DBN), 3,36-3,62 (2H, m, S—CH₂—, H-2), 4.62 (1H, d, CH, H-7), 5.01 (1H, d, CH, H-6), 5.56 (1H, dq, =CH—CH₃ PACA), 6.39 (1H, d(m), CH=PACA)

The invention claimed is:

1. A process for the production of cefprozil or cefprozil in the form of a monohydrate comprising the steps
    A1) reacting the compound of formula

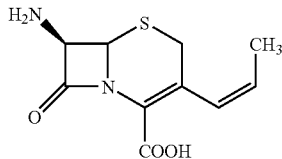

III in the form of a salt with an amidine or a guanidine with a mixed carboxylic acid anhydride of an α-amino-p-hydroxyphenylacetic acid, and
   B1) isolating ceprozil from the reaction mixture obtained in step A1); and optionally
   C1) cefprozil isolated in step B1) into ceprozil in the form of a monohydrate.

2. A process for the production of cefprozil in the form of a monohydrate which comprises the steps
   A2) producing a mixed carboxylic acid anhydride by acylating a vinyl substituted α-amino-p-hydroxyphenylacetic acid with an appropriate acylating agent.
   B2) reacting a mixed carboxylic acid anhydride obtainable in step A2) with a compound of formula

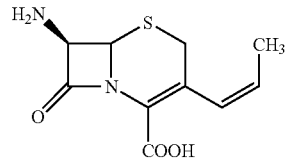

III in the form of a salt with an amidine or a guanidine.
   C3) deprotecting the cefprozil in protected form obtained in step B2,
   D3) isolating cefprozil- N,N-dimethylformamide solvate by crystallization, and
   E3) converting cefprozil- N,N-dimethylformamide solvate obtained III step D3) into cefprozil in the form of a monohydrate.

3. A process according to claim 2 wherein the cefprozil- N,N-dimethylformamide solvate is a 1/1.5 N,N-dimethylformamide solvate.

4. A compound of the formula

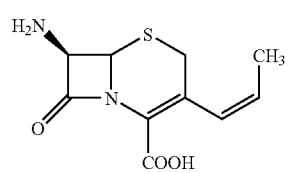

III in the form of a salt with an amidine or a guanidine or an acid addition salt thereof.

5. A compound according to claim 4 of formula

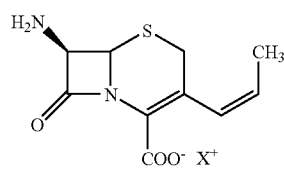

I where in
   X is a group of formula

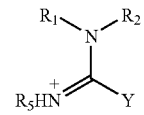

II

Y is
   a) a group of formula -NR₃R₄ and
      a1) R₁ to R₅ are the same or different and are independently of each other hydrogen, alkyl or aryl; or
      a2) two of the substituents R₁, R₂ and R₅, and/or R₃ and R₄ together form a —(CH₂)₂— or —(CH₂)₃— group; and the other substituents R₁ to R₅ are as defined above; or b) together with $R_2$ form a —$(CH_2)_3$— or —$(CH_2)_5$— group, and $R_1$ and $R_5$ together form a —$(CH_2)_3$— group.

6. A compound according to claim 4, wherein the compound of formula III is in the form of a salt with an amidine or guanidine selected from the group consisting of tetramethylguanidine, 1.8-diaza-bicylo-(5.4.0)undec-7-ene and 1.5-diaza-bicylo-(4.3.0)non-5-ene.

7. A process for the production of a compound of formula III in the form of a salt with an amidine or guanidine comprising:

suspending a compound of formula

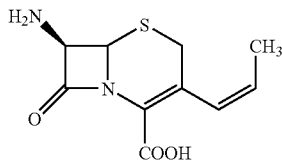

III in an appropriate solvent adding an amidine or guanidine and isolating the compound of formula III in the form of a salt with an amidine or a guanidine.

8. A process for the production of cefprozil comprising the step of acylating the amine group in position 7 of the compound of formula

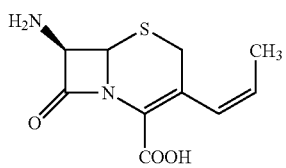

III in the form of a salt with an amidine or guanidine with a mixed carboxylic acid anhydride of an α-amino-p-hydroxyphenyl acetic acid.

9. The process according to claim 8, wherein the compound of formula

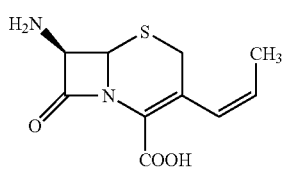

III 10 in the form of a salt with an amidine or guanidine is a compound of formula

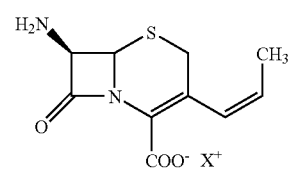

I wherein
X is a group of formula

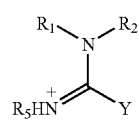

II

Y is
  a) a group of formula -$NR_3R_4$ and
    a1) $R_1$ to $R_5$ are the same or different and are independently of each other hydrogen, alkyl or aryl; or
    a2) two of the substituents $R_1$, $R_2$ and $R_5$, and/or $R_3$ and $R_4$ together form a —$(CH_2)_2$— or —$(CH_2)_3$ — group; and the other substituents $R_1$ to $R_5$ are as defined above; or
  b) together with $R_2$ form a —$(CH_2)_3$— or —$(CH_2)_5$— group, and $R_1$ and $R_5$ together form a —$(CH_2)_3$— group.

10. The process according to claim 8, wherein the amidine or guanidine is selected from the group consisting of tetramethylguanidine, 1.8-diaza-bicylo-(5.4.0)undec-7-ene and 1.5-diaza-bicylo-(4.3.0)non-5-ene.

* * * * *